United States Patent [19]

Schoengen et al.

[11] Patent Number: 4,578,501

[45] Date of Patent: Mar. 25, 1986

[54] PREPARATION OF TEREPHTHALIC ACID FROM A CRUDE DIMETHYL TEREPHTHALATE

[75] Inventors: Anton Schoengen, Witten; Georg Schreiber, Cologne; Heinz Schroeder, Dortmund-Syburg, all of Fed. Rep. of Germany

[73] Assignee: Dynamit Nobel Aktiengesellschaft, Troisdorf, Fed. Rep. of Germany

[21] Appl. No.: 141,572

[22] Filed: Apr. 18, 1980

Related U.S. Application Data

[63] Continuation-in-part of Ser. No. 79,253, Sep. 27, 1979, Pat. No. 4,302,595.

[30] Foreign Application Priority Data

Apr. 21, 1979 [DE] Fed. Rep. of Germany ....... 2916197
Mar. 27, 1980 [DE] Fed. Rep. of Germany ....... 3011858

[51] Int. Cl.$^4$ .................... C07C 67/39; C07C 51/09; B01D 3/14; B01D 9/02
[52] U.S. Cl. .................................. 560/77; 562/483; 203/48; 203/73; 203/DIG. 6; 203/DIG. 8
[58] Field of Search .................... 562/483; 203/48, 73, 203/DIG. 6, DIG. 8; 560/77

[56] References Cited

U.S. PATENT DOCUMENTS 2,646,393 7/1953 Hughes et al. ......................... 560/78
2,992,168 7/1961 Wilson et al. ......................... 560/78
3,399,227 8/1968 Tapulionis ............................ 560/78
4,302,595 11/1981 Svhoengen et al. ................. 562/483

FOREIGN PATENT DOCUMENTS 19338 5/1981 Japan .
1130695 3/1967 United Kingdom .
1344383 1/1974 United Kingdom .

OTHER PUBLICATIONS

Kirk-Othmer, "Encyclopedia of Chemical Technology", 2nd Ed., vol. 6, 1965, pp. 482 and 492–493.

Primary Examiner—Natalie Trousof
Assistant Examiner—L. Hendriksen
Attorney, Agent, or Firm—Antonelli, Terry & Wands

[57] ABSTRACT

A process for the production of a crude dimethyl terephthalate suitable for hydrolyzing into a fiber grade terephthalic acid involves separating a crude ester obtained from the production of dimethyl terephthalate by the Witten process by vacuum distillation at elevated pressure in a three-column series arranged distillation system. In the first distillation column of the system the crude is separated into a methyl p-toluate-rich fraction as head product; in a second column of the series, into a fraction rich in methyl ester of terephthalaldehydic acid as head product; and in a third distillation column, a crude dimethyl terephthalate fraction. The crude dimethyl terephthalate fraction has a methyl ester of terephthalaldehydic acid content of 0.01–0.1% by weight as a head product.

4 Claims, 1 Drawing Figure

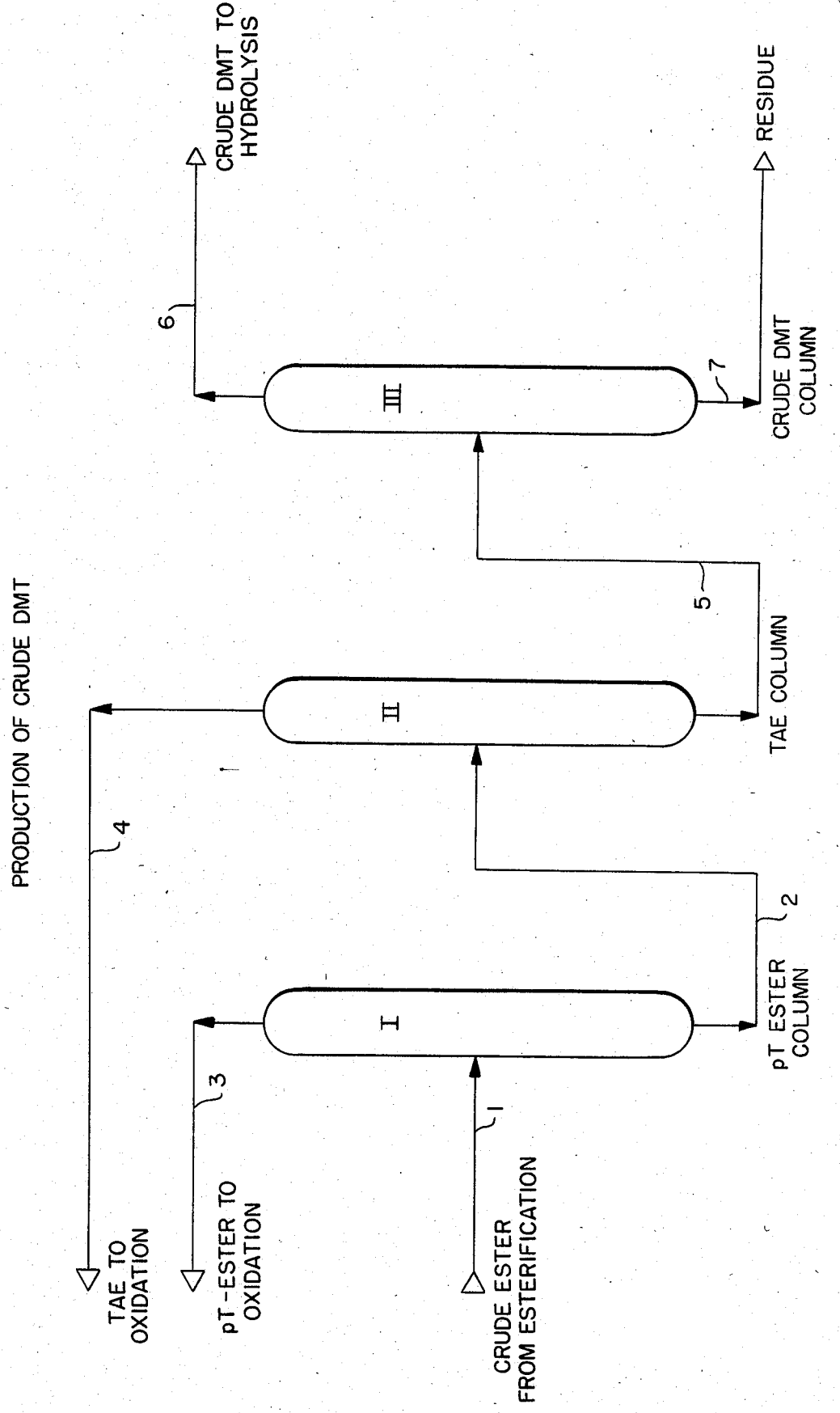

PREPARATION OF TEREPHTHALIC ACID FROM A CRUDE DIMETHYL TEREPHTHALATE

This application is a continuation-in-part application of Ser. No. 079,253, filed Sept. 27, 1979 now U.S. Pat. No. 4,302,595.

This invention relates to the preparation of terephthalic acid from a crude dimethyl terephthalate and more particularly to a process for processing an intermediate stage crude dimethyl terephthalate by distillation to provide a crude dimethyl terephthalate product that can be hydrolyzed to provide a fiber grade terephtalic acid.

In the preparation of terephthalic acie (TPA) from alkyl terephthalate by reacting alkyl terephthalate in water under increased pressure and at an increased temperature with a weight ratio of between 3:1 and 0.1:1 until hydrolysis is essentially completed, and by separating the terephthalic acid from the thus-obtained hydrolysate, the low- and high-boiling impurities in the dimethyl terephthalate (DMT) employed as the starting material for the hydrolysis determine the quality of the TPA formed by the hydrolysis, if these by-products, optionally after conversion under the hydrolysis conditions, are precipitated together with the thus-obtained TPA and cannot be removed by separation of the mother liquor and/or by recrystallization.

Crude dimethyl terephthalate produced according to the Witten DMT or Katzschmann process (cf. *Hydrocarbon Processing*, November 1976, p. 131) from the so-called crude ester by distillation in large-scale technical plants as an intermediate for further processing to dimethyl terephthalate contains, in addition to the isomers dimethyl orthophthalate and dimethyl isophthalate (DMO, DMI), the methyl ester of terephthaldehydic acid (TAE) as the primary impurities.

TAE is converted to terephthalaldehydic acid (TAA) in the hydrolysis of crude DMT and is then present with a content corresponding to the TAE content, in addition to the thus-formed TPA and the other by-products. TAA is precipitated together with TPA with the occurrence of an occlusion of TAA into the TPA crystal lattice. Since TAA is an impurity disadvantageous for the processing of TPA to polyesters for threads and fibers, it has been considered important to limit the TAA content in the TPA final product to values of below 0.01% by weight.

The lowering of the TAA content in a crude or impure TPA obtained by direct oxidation of p-xylene with atmospheric oxygen in a solvent is effected, for example, in an aqueous solution by suitable chemical conversion of the carbonyl function of TAA with hydrogen (as described in U.S. Pat. No. 3,584,039). The removal of TAA by chemical as well as physical methods is very energy-consuming due to the low solubility or TPA in water or other suitable solvents and imposes stringent requirements of the resistivity of the materials for the containers wherein these operations are carried out.

The invention starts at this stage of development and is directed to the object of reducing the TAE content in the crude dimethyl terephthalate for the production of TPA with a tolerable expenditure of energy and auxiliary agents to such an extent that a TAA content of maximally 0.01% by weight is now exceeded in the TPA obtained by the hydrolysis, and without requiring an additional purification step to reduce the TAA content in the thus-formed TPA.

The subject matter of the parent patent application Ser. No. 079,253 is a process for the production of terephthalic acid (TPA) from a crude dimethyl terephthalate (DMT) obtained as an intermediate product in the production of dimethyl terephthalate in the Witten process.

The present invention likewise makes use of the apparatus and reaction procedures heretofore disclosed in the parent application (this disclosure of the apparatus and reaction procedures is incorporated by reference into the description of the present invention) and is especially directed to a distillation procedure wherein a crude DMT is produced having a content of 0.01-0.1% by weight of TAE and is utilized in the hydrolysis stage to provide high quality TPA.

The object of the invention is the production of a crude DMT containing between 0.01 and 0.1% by weight of TAE in the hydrolysis process, starting with the intermediate crude DMT having a limited content of oxidation intermediates and other by-products.

This object is attained in the present invention by subjecting a crude ester, as obtained in the Witten or Katzschmann process after esterification of the oxidized product with methanol in the gaseous phase at elevated pressure and elevated temperature, to a distillation in a three-column system shown in the single FIGURE of the accompanying drawing and under the conditions hereinafter specified. This system consists of three series-connected columns denoted, in the sequence, as the methyl p-toluate (PTE) column, the TAE column and the crude DMT column.

In DMT plants, the configuration of which corresponds, for example, to the flow scheme shown in *Hydrocarbon Processing*, November 1975, p. 131, the TAE column will be connected downstream of the crude DMT column. In such a configuration the TAE-containing crude DMT is fed to the TAE column, a TAE-enriched fraction is withdrawn as the head product which can be recycled into the oxidation stages and an extensively TAE-free crude DMT is obtained as the sump product.

It has been found as pointed out in the parent application that it is possible, with the configuration of the three distillation columns according to the single FIGURE of this application, to lower the TAE content to values of 0.1% by weight and even down to about 0.01% by weight, with still tolerable energy expenditure, in spite of the fact that the boiling point of TAE is very close to that of DMT, under the pressure and temperature conditions utilized in accordance with this invention.

More particularly, this invention is directed to a process for the production of fiber grade terephthalic acid from dimethyl terephthalate as the intermediate product by oxidation of p-xylene and/or methyl p-toluate with oxygen-containing gases in the presence of heavy-metal-containing oxidation catalysts at elevated temperature and elevated pressure by esterification of the oxidation mixture with methanol at elevated temperature and elevated pressure and by distillatory separation of the crude ester into a methyl p-toluate-rich fraction to by recycled into the oxidation and a residual fraction as well as a crude dimethyl terephthalate having a limited content of oxidation intermediates and other by-products, by continuous hydrolysis of the crude dimethyl terephthalate with water at a mass ratio of crude dimethyl terephthalate to water of between 3:1 and 0.1:1 and at a temperature of between 350° C. and 140° C. and at a pressure required to maintain the liquid phase to produce a reaction mixture containing crystalline fiber grade terephthalic acid, by recrystallization of the terephthalic acid at a temperature of between 300° C. and 150° C., by replacement of the mother liquor by demineralized water, and obtaining the terephthalic acid from the reaction mixture, the two-stage conductance of the hydrolysis being effected by:

(a) separation of the reaction mixture after the first hydrolysis stage into a thickened suspension of solid terephthalic acid and mother liquor and a liquid phase containing the residual mother liquor, (b) continuous dilution and quantitative replacement of the mother liquor in the suspension by demineralized water conducted countercurrently to the crystallized terephthalic acid in the second stage of hydrolysis, (c) single- or multi-stage expansion of the thus-obtained suspension of demineralized water and terephthalic acid and obtaining of the terephthalic acid by means of a solid-liquid separating operation, and (d) cooling of the combined mother liquors according to stages (a) and (b) to such an extent that still dissolved terephthalic acid, as well as by-products, are presipitated separately or together, separating of these as solid substances, and optionally transferring out isomers of terephthalic acid and separation of the liquid phase by distillation into a methanol-water mixture discharged overhead as well as an aqueous phase obtained as the sump product, part of which is transferred out and the remaining part being combined with the separated solids and recycled into the first hydrolysis stage after reheating; the distillory separation of the crude ester being effected by vacuum distillation at elevated temperature in a three-column series-arranged distillation system wherein the crude ester is separated into a methyl p-toluate-rich fraction as head product of a methyl p-toluate first column, into a fraction rich in methyl ester of terephthalaldehydic acid as head product of the second column for distilling the terephthalaldehydic acid ester as well as a purified crude dimethyl terephthalate fraction with a methyl ester of terephthalaldehydic acid content of 0.01–0.1% by weight as head product and a residual fraction as the sump product of a crude dimethyl terephthalate third column.

In the single FIGURE, a DMT-containing crude ester is introduced via line 1 into the PTE distillation column I from which a head product containing PTE exits through line 3 and a sump product basically containing DMT is removed via line 2. This sump product enters the TAE distillation column II. A head product of the TAE column exits through line 4 and a sump product is passed via line 5 to the crude DMT distillation column III. The head product containing the purified DMT for hydrolysis exits through line 6 and the sump product containing the residue of the distillation is removed through line 7.

This configuration also has the advantage that, in the subsequently arranged crude DMT column, the crude DMT is withdrawn as the head product, and the high-boiling components are withdrawn as the sump product, in contradistinction to the configuration wherein the TAE column is the last column of the flow scheme and wherein the TAE-rich fraction is discharged as the head product and the crude DMT as the sump product.

According to this invention, the process of obtaining the purified crude DMT is carried out with a vacuum at the head of the PTE column of about 0.1 bar, with a head temperature of about 140° C., with a reflux ratio R=0.5:1 to 3:1, and at a sump temperature of about 200° C.

In the TAE column the process is conducted with a vacuum at the head of between 0.015 and 0.1 bar, a head temperature of between 130° and 190° C., a reflux ratio R of 3:1 to 15:1, and a sump temperature of about 150°–200° C. Especially suitable for the TAE distillation are columns low of pressure loss, e.g. columns having suitable packings or fillings.

In the crude DMT column the process is effected with a vacuum at the head of 0.03 to 0.1 bar, a head temperature corresponding to the pressure selected, a reflux ratio R of 0.1:1 to 1:1, and a sump temperature of about 240° C.

Heretofore, i.e. prior to the invention as heretofore described in the parent application, only such sump pressures were utilized in the distillation of the crude ester that there was practically no separation of DMT and TAE.

It has further been found that the boiling curve and dew curve of the system DMT-TAE are so far apart at the pressures employed according to this invention that an economical separation in distillation columns is made possible. In this connection, one had to keep in mind, in particular, that relatively low boiling pressures are ambient in the sump section of the TAE column, leading to the use of columns with low pressure losses as proposed by this invention.

Columns having orderly packings and/or trickling packs are especially suitable.

By means of the distillation in accordance with the invention, the production of a sufficiently pure crude DMT as intermediate product becomes possible in a novel, surprising fashion. It thus becomes feasible to conduct the direct crystallization of the TPA produced by hydrolysis of the crude DMT without additional purification operations.

The process of this invention is illustrated in the following Examples 1 and 2.

The indicated mass streams are expressed as parts by weight per hour; the compositions are expressed in percent by weight.

The following is a compilation of the chemical abbreviations employed in the examples:
DMI=1,3-dimethyl phthalate
DMO=1,2-dimethyl phthalate
DMT=dimethyl terephthalate
HB=high-boiling components
BME=methyl benzoate
MMT=monomethyl terephthalate
TPA=terephthalic acid
TAE=terephthalaldehydic acid methyl ester
PTA=p-toluic acid
PTE=methyl p-toluate

EXAMPLE 1

33,022 kg/h of DMT-containing crude ester obtained from a Witten process plant is subjected to a continuous distillation in the PTE column (I) with 30 practical plates, thus obtaining 11,243 kg/h of head product and 20,376 kg/h as sump product.

Vacuum at the head 0.1 bar; head temperature 143° C.; sump temperature 215° C.; reflux ratio 0.5:1.

Composition of the initial DMT containing crude ester, head product and sump product:

|  | Crude Ester % | Head Product % | Sump Product % |
| --- | --- | --- | --- |
| HB | 5.75 | — | 9.32 |
| TPA | 0.15 | — | 0.24 |
| MMT | 0.92 | — | 1.49 |
| DMO  <br> DMI  <br> DMT | 53.55 | 1.00 | 86.07 |
| TAE | 1.83 | 2.00 | 1.87 |
| PTA | 0.46 | — | 0.75 |
| PTE | 32.92 | 89.00 | 0.06 |
| BME | 3.29 | 7.50 | — |
| p-xylene | 0.17 | 0.05 | — |
| Water | 0.05 | — | — |
| Methanol | 0.53 | — | — |
| Methyl acetate | 0.05 | — | — |
| Σ of Secondary Components | 0.33 | 0.45 | 0.20 |

The sump product is subjected to a further distillation in the TAE column, thus obtaining 2,671 kg/h of head product and 17,692 kg/h of sump product.

Vacuum at the head 0.02 bar; head temperature 152° C.; sump temperature 189° C.; reflux ratio 12:1.

Composition of head product and sump product:

|  | Head Product % | Sump Product % |
| --- | --- | --- |
| HB | — | 10.73 |
| TPA | — | 0.28 |
| MMT | — | 1.72 |
| DMO  <br> DMI  <br> DMT | 81.58 | 86.76 |
| TAE | 14.13 | 0.01 |
| PTA | 3.79 | 0.28 |
| PTE | 0.30 | 0.02 |
| Σ of Secondary Components | 0.20 | 0.20 |

The sump product is subjected to a further distillation in the third crude DMT column, thus forming 15,199 kg/h of head product and 2,480 kg/h of sump product. Head vacuum 0.05 bar; head temperature 184° C.; sump temperature 240° C.; reflux ratio 0.3:1.

Composition of the head product and sump product:

|  | Head Product % | Sump Product % |
| --- | --- | --- |
| HB | — | 76.56 |
| TPA | 0.05 | 1.69 |
| MMT | 0.19 | 11.11 |
| DMO  <br> DMI  <br> DMT | 99.21 | 10.42 |
| TAE | 0.01 | 0.02 |
| PTA | 0.33 | — |
| PTE | 0.01 | — |
| Σ of Secondary Components | 0.20 | 0.20 |

EXAMPLE 2 (Comparative Example)

(Same conditions as columns I and III in Example 1 with the omission of column II.)

33,022 kg/h of crude ester are subjected to a distillation in a PTE column under the following conditions: vacuum at the head 0.1 bar; head temperature 143° C.; sump temperature 215° C.; reflux ratio 0.5:1, thus obtaining 11,243 kg/h of head product and 20,376 kg/h of sump product.

Composition of crude ester, head product and sump product:

|  | Crude Ester % | Head Product % | Sump Product % |
| --- | --- | --- | --- |
| HB | 5.75 | — | 9.32 |
| TPA | 0.15 | — | 0.24 |
| MMT | 0.92 | — | 1.49 |
| DMO  <br> DMI  <br> DMT | 53.55 | 1.00 | 86.07 |
| TAE | 1.83 | 2.00 | 1.87 |
| PTA | 0.46 | — | 0.75 |
| PTE | 32.92 | 89.00 | 0.06 |
| BME | 3.29 | 7.50 | — |
| p-xylene | 0.17 | 0.05 | — |
| Water | 0.05 | — | — |
| Methanol | 0.53 | — | — |
| Methyl acetate | 0.05 | — | — |
| Σ of Secondary Components | 0.33 | 0.45 | 0.20 |

The sump product is subjected, in a substantially connected crude DMT column, to a further distillation under the following conditions: vacuum at the head 0.05 bar; head temperature 184° C.; sump temeprature 240° C.; reflux ratio 0.3:1, thus obtaining 17,883 kg/h of head product and 2,480 kg/h of sump product.

Composition of head product and sump product:

|  | Head Product % | Sump Product % |
| --- | --- | --- |
| HB | — | 76.56 |
| TPA | 0.04 | 1.69 |
| MMT | 0.16 | 11.09 |
| DMO  <br> DMI  <br> DMT | 96.56 | 10.45 |
| TAE | 2.13 | 0.01 |
| PTA | 0.85 | — |
| PTE | 0.06 | — |
| Σ of Secondary Components | 0.20 | 0.20 |

What is claimed is:

1. A process for the production of fiber grade terephthalic acid from dimethyl terephthalate as the intermediate product by oxidation of p-xylene and/or methyl p-toluate with oxygen-containing gases in the presence of heavy-metal-containing oxidation catalysts at elevated temperature and elevated pressure, by esterification of the oxidation mixture with methanol at elevated temperature and elevated pressure, and by distillatory separation of the crude ester into a methyl p-toluate-rich fraction recycled into the oxidation and a residual fraction, as well as into a crude dimethyl terephthalate having a limited content of oxidation intermediates and other by-products, by continuous hydrolysis of the crude dimethyl terephthalate with water at a mass ratio of crude dimethyl terephthalate to water of between 3:1 and 0.1:1 and at temperatures of between 350° C. and 140° C. and at the pressure required to maintain the liquid phase to produce a reaction mixture containing crystalline fiber grade terephthalic acid, by recrystallization of the terephthalic acid at temperatures of between 300° C. and 150° C., replacement of the mother liquor by demineralized water, and obtaining the terephthalic acid from the reaction mixture, two-stage conductance of the hydrolysis being effected by:
  (a) separation of the reaction mixture after the first hydrolysis stage into a thickened suspension of solid terephthalic acid and mother liquor and a liquid phase containing the residual mother liquor,
  (b) continuous dilution and quantitative replacement of the mother liquor in the suspension by demineralized water conducted counter-currently to the crystallized terephthalic acid in the second hydrolysis state,
  (c) single- or multi-stage expansion of the thus-obtained suspension of demineralized water and terephthalic acid and obtaining of the terephthalic acid by means of a solid-liquid separating operation,
  (d) cooling of the combined mother liquors according to stages (a) and (b) to such an extent that still dissolved terephthalic acid, as well as by-products, are precipitated separately or together thereby separating as solid substances; the distillatory separation of the crude ester being effected by vacuum distillation at elevated temperature in a three-column series-arranged distillation system wherein the crude ester is separated into a methyl p-toluate-rich fraction as head product of a methyl p-toluate first column, into a fraction rich in methyl ester of terephthalaldehydic acid as head product of the second column for distilling the terephthalaldehydic acid ester as well as a purified crude dimethyl terephthalate fraction with a methyl ester of terephthalaldehydic acid content of 0.01–0.1% by weight as head product and a residual fraction as the sump product of a crude dimethyl terephthalate third column.

2. A process according to claim 1, wherein the crude ester is separated by vacuum distillation at elevated temperature in a 3-column system and in the methyl p-toluate column at the head a pressure is set of about 0.1 bar and a temperature of about 140° C. with a reflux ratio of 0.5:1 to 3:1 and in the sump a temperature is set of about 200° C., the head product is recycled into the oxidation, and the sump product of the methyl p-toluate column is introduced into the subsequently connected terephthalaldehydic acid methyl ester column, a pressure is set in the terephthalaldehydic acid methyl ester column at the head of 0.015 to 0.1 bar, a temperature of 130° to 190° C. with a reflux ratio of 3:1 to 15:1, and in the sump a temperature is set of 150° to 200° C., the head product is recycled into the oxidation, and the sump product of the terephthalaldehydic acid methyl ester column is introduced into the subsequently connected crude dimethyl terephthalate column and, in the crude dimethyl terephthalate column at the head a pressure is set of 0.03 to 0.1 bar, a head temperature which corresponds to the selected pressure, with a reflux ratio of 0.1:1 to 1:1 and a sump temperature is set of about 240° C., the purified head product is fed to the hydrolysis, and the sump product is transferred out.

3. A process for the production of a crude dimethyl terephthalate to by hydrolyzed into a fiber grade terephthalic acid from a crude dimethyl terephthalate ester obtained from the production of dimethyl terephthalate by the Witten process wherein p-xylene and/or methyl p-toluate are oxidized with oxygen-containing gas in the presence of heavy-metal-containing oxidation catalysts at elevated temperature and elevated pressure, and the resulting oxidation mixture is subject to esterification with methanol at elevated temperature and elevated pressure to produce said crude ester, which comprises separating the crude ester by vacuum distillation at elevated temperature in a three-column series-arranged distillation system into a methyl p-toluate-rich fraction as head product of a first distillation column, into a fraction rich in methyl ester of terephthalaldehydic acid as head product of a second column and a crude dimethyl terephthalate fraction with a methyl ester of terephthalaldehydic acid content of 0.01–0.1% by weight as head product suitable for hydrolysis into a fiber grade terephthalic acid and a residual fraction as the sump product in the third distillation column.

4. A process according to claim 3, wherein in the first column a pressure is set at the head of about 0.1 bar and a temperature of about 140° C. with a reflux ratio of 0.5:1 to 3:1 and in the sump a temperature is set of about 200° C., with the head product being recycled into the oxidation stage of the Witten process and the sump product of the first column being introduced into the subsequently connected second column; a pressure is set in the second column at the head of 0.015 to 0.1 bar with a temperature of 130° to 190° C. and with a reflux ratio of 3:1 to 150:1, and in the sump of the second column a temperature is set of 150° to 200° C., the head product being recycled into the oxidation stage and the sump product of the second column being introduced into the subsequently connected third column; and in the third column at the head a pressure is set of 0.03 to 0.1 bar with a head temperature which corresponds to the selected head pressure and with a reflux ratio of 0.1:1 to 1:1 and the sump temperature of the third column is set at about 240° C., the head product being of sufficient purity to be fed to a hydrolysis unit, and the sump product being discharged from the system.

* * * * *